(12) United States Patent
Lee (10) Patent No.: US 11,724,122 B2
(45) Date of Patent: Aug. 15, 2023

(54) WEARABLE MULTI-WAVELENGTH LASER THERAPY DEVICE THAT IS EFFECTIVE IN TREATING JOINT PAIN AND ARTHRITIS BY A SLELECTIVE ACTION OF CELL REGENERATION AND BLOOD FLOW IMPROVEMENT

(71) Applicant: WELLSCARE CO., LTD, Seoul (KR)

(72) Inventor: Sung Won Lee, Yongin-si (KR)

(73) Assignee: WELLSCARE CO., LTD, Seoul (KR)

( * ) Notice: Subject to any disclaimer, the term of this patent is extended or adjusted under 35 U.S.C. 154(b) by 0 days.

(21) Appl. No.: 17/477,143

(22) Filed: Sep. 16, 2021

(65) Prior Publication Data

US 2022/0001198 A1 Jan. 6, 2022

Related U.S. Application Data

(63) Continuation of application No. 16/074,211, filed as application No. PCT/KR2017/005059 on May 16, 2017, now Pat. No. 11,154,723.

(30) Foreign Application Priority Data

Nov. 22, 2016 (KR) .......... 10-2016-0155918
May 15, 2017 (KR) .......... 10-2017-0059923

(51) Int. Cl.
*A61N 5/06* (2006.01)
*A61N 5/067* (2006.01)

(52) U.S. Cl.
CPC ......... *A61N 5/0616* (2013.01); *A61N 5/0619* (2013.01); *A61N 5/067* (2021.08); *A61N 2005/0645* (2013.01); *A61N 2005/0651* (2013.01)

(58) Field of Classification Search
CPC .... A61N 5/0616; A61N 5/0619; A61N 5/067; A61N 2005/0645; A61N 2005/0651; A61N 2005/0659; A61N 7/00; A61N 2005/0663; A61N 5/06; A61N 5/0613;
(Continued)

(56) References Cited

U.S. PATENT DOCUMENTS

| 5,616,140 A | 4/1997 | Prescott |
| 6,063,108 A | 5/2000 | Salansky et al. |
| 6,814,706 B2 | 11/2004 | Barton et al. |

(Continued)

FOREIGN PATENT DOCUMENTS

| EP | 1839705 A1 | 10/2007 |
| EP | 2446865 A1 | 5/2012 |

(Continued)

*Primary Examiner* — Joseph M Dietrich
*Assistant Examiner* — Michael T. Holtzclaw
(74) *Attorney, Agent, or Firm* — Bridgeway IP Law Group, PLLC; Sang Ho Lee; Hyun Woo Shin (57) ABSTRACT

Provided is a laser patch, and the laser patch includes: a patch body having a through hole for laser transmission; a circuit substrate disposed in the patch body; a built-in battery disposed, facing the circuit substrate, in the patch body; a laser diode element electrically connected to the circuit substrate and emitting a low-output laser beam to the outside of the patch body by using its own power coming from the built-in battery; and a charging terminal provided in the patch body for selectively supplying electricity to the built-in battery from an external charger.

6 Claims, 8 Drawing Sheets

(58) Field of Classification Search
CPC .. A61N 2005/0627; A61B 2017/00734; A61B 2018/00791; A61B 2090/065; A61B 5/01
See application file for complete search history.

(56) References Cited

U.S. PATENT DOCUMENTS

| | | | |
|---|---|---|---|
| 9,636,522 B2* | 5/2017 | Oversluizen | A61N 5/0616 |
| 2005/0177093 A1 | 8/2005 | Barry et al. | |
| 2005/0187597 A1 | 8/2005 | Vanderschuit | |
| 2010/0100160 A1 | 4/2010 | Edman et al. | |
| 2012/0109233 A1 | 5/2012 | Lee et al. | |
| 2014/0012353 A1 | 1/2014 | Prescott | |
| 2014/0094879 A1* | 4/2014 | Van Os | A61N 5/0613 |
| | | | 607/88 |
| 2014/0157174 A1 | 6/2014 | Deroberts | |
| 2014/0277298 A1* | 9/2014 | Tapper | A61N 5/0616 |
| | | | 607/91 |
| 2014/0303692 A1 | 10/2014 | Pignatelli et al. | |
| 2016/0129279 A1 | 5/2016 | Ferolito | |
| 2016/0129281 A1* | 5/2016 | Kim | A61N 5/0619 |
| | | | 607/90 |

FOREIGN PATENT DOCUMENTS

| | | |
|---|---|---|
| JP | 1989-136668 A | 5/1989 |
| JP | 1997-201422 A | 8/1997 |
| JP | 2000-342701 A | 12/2000 |
| JP | 2006-239213 A | 9/2006 |
| JP | 2013-094429 A | 5/2013 |
| JP | 2016-501596 A | 1/2016 |
| JP | 2016-052505 A | 4/2016 |
| KR | 10-2003-0041703 A | 5/2003 |
| KR | 10-0915320 B1 | 9/2009 |
| KR | 10-1181580 B1 | 9/2012 |
| WO | 2016-060289 A1 | 4/2016 |

* cited by examiner

WEARABLE MULTI-WAVELENGTH LASER THERAPY DEVICE THAT IS EFFECTIVE IN TREATING JOINT PAIN AND ARTHRITIS BY A SLELECTIVE ACTION OF CELL REGENERATION AND BLOOD FLOW IMPROVEMENT

CROSS REFERENCE TO RELATED APPLICATIONS

This application is a Continuation Application of the U.S. application Ser. No. 16/074,211 filed on Jul. 31, 2018, which is a national-stage under 35 USC 371 of PCT/KR2017/005059 filed on May 16, 2017, and claims priority under 35 U.S.C. § 119 to Korean Patent Applications Nos. 10-2016-0155918 filed on Nov. 22, 2016, and 10-2017-0059923 filed on May 15, 2017, in the Korean Intellectual Property Office, the entire contents of which are hereby incorporated by reference.

TECHNICAL FIELD

The present invention relates to a laser patch and a laser patch treatment set including the same, and more particularly, to a laser patch configured to include a built-in battery to be repeatedly used through charging and to have a relatively small thin plate shape such that the laser patches may be combined to be selectively used in local areas and a laser patch treatment set including the laser patch.

BACKGROUND ART

Generally, external preparations called patches or pain relief patches are medications which are attached to a human body to relieve pain of a diseased area. Patches have a bandage form to which a patch solution mixed with an adhesive solution is applied and are attached to a diseased area to be used. Patches include warm packs, cold packs, and the like according to ingredients or types of applied patch solutions. Recently, patches including a magnet, an acupuncture needle, or the like disposed in a center for further improving blood flow have been provided.

However, in the above-described patches, side effects such as skin trouble caused by applied adhesive solutions or patch solutions, lack of air circulation during attachment, or the like, serious or slight burns, skin rashes, sores, and the like occur. Particularly, due to such side effects, it is difficult for people who inherently have delicate skin or children to use such patches. Also, since general patches provide a limitative effect which is not a fundamental therapy and most are used once and discarded, there are disadvantages such as the cost burden for long-term use and not being eco-friendly.

Meanwhile, it is well known through a variety of clinical data that low level lasers (LLLs) provides a variety of effects such as pain relief, blood flow improvement, blood flow strengthening, skin regeneration, cell activation, lipolysis, cell stimulation, and the like according to particular wavelength ranges. Particularly, in comparison to high level lasers used for destruction, intentional injuries, or necrosis of skin tissue, LLLs are relatively safe and have functions of boosting metabolism, activating cells, and increasing a level of immunity so as to restore injured cell tissue. Particularly, it is known that when LLLs of a particular wavelength range are selectively emitted toward acupoints on a body, effects like those of acupuncture or moxa cautery treatment are provided such that pain of skin or muscles is relieved and complete recovery of a diseased area is promoted.

DISCLOSURE OF INVENTION

Technical Problem

The present invention is directed to providing a laser patch and a laser patch treatment set including the same using a low level laser (LLL) light source which provides high treatment effects without the skin trouble of general patches such as skin rashes, occurrence of allergies, burns, and the like.

The present invention is directed to providing a laser patch and a laser patch treatment set including the same configured to have a patch structure including relatively small thin plate-shaped patches to perform treatment in local areas such that a user may combine and use laser patches according to a necessary treatment type and desired local areas.

The present invention is directed to providing a laser patch and a laser patch treatment set including the same which include laser patches to which a built-in battery capable of being repeatedly used through electrical charging is applied such that a user may perform self-treatment with the same effects at no additional cost for a long time and resources may be prevented from being wasted to be eco-friendly in comparison to general patch or pain relief patches.

The present invention is directed to providing a laser patch and a laser patch treatment set including the same which are configured to connect to a user terminal on which an application, which guides a user of the laser patch with an accurate procedure for acupuncture or moxa cautery treatment, which is a Korean medicine treatment, is loaded such that an ordinary user who has no or lacks Korean medicine treatment knowledge may also simply and accurately perform Korean medicine self-treatment.

Technical Solution

One aspect of the present invention provides a laser patch including a patch body which comprises a through hole for transmitting a laser, a circuit board disposed inside the patch body, a built-in battery disposed in the patch body to be opposite the circuit board, a laser diode device which is electrically connected to the circuit board and emits a low level laser (LLL) toward the outside of the patch body by using own power from the built-in battery, and a charging terminal provided in the patch body for optional power supply to the built-in battery from an external charger.

Another aspect of the present invention provides a laser patch which is an LLL patch having at least one purpose of pain relief, blood flow improvement, cell activation, cell generation, lymph node stimulation, and edema relief. The laser patch includes a patch body having a plate shape which includes a through hole for transmitting a laser, a circuit board disposed in the patch body, a built-in battery disposed in the patch body, and a laser diode device which is electrically connected to the circuit board, receives power from the built-in battery, and emits an LLL toward the outside of the patch body. Here, the laser diode device includes a first device which emits an LLL having a wavelength range of 630 nm to 680 nm and a second device which emits an LLL having a wavelength range of 780 nm to 990 nm.

Still another aspect of the present invention provides a laser patch treatment set including a laser patch which comprises a built-in battery capable of being repeatedly charged and emits an LLL by using own power of the built-in battery and a user terminal which is connected to the laser patch by using a communication technology and on which an application for guiding a user with use information of the laser patch is loaded.

Advantageous Effects

According to embodiments of the present invention, a laser patch and a laser patch treatment set including the same includes relatively small plate-shaped laser patches to perform treatment in a local area such that the patches can be appropriately combined to fit a necessary treatment type and a desired local area by a user.

According to embodiments of the present invention, a laser patch and a laser patch treatment set including the same can perform treatments for pain relief, blood flow improvement, blood flow strengthening, skin regeneration, cell activation, lipolysis, cell stimulation, and the like without the skin trouble such as a skin rash, an allergy, a burn, and the like which are problems caused by an adhesive and a patch in comparison to general patches or pain relief patches.

According to the embodiments of the present invention, a laser patch and a laser patch treatment set including the same can allow a user to perform self-treatment with the same effect at no additional cost for a long time and prevent resource waste to be eco-friendly in comparison to general patches or pain relief patches.

According to embodiments of the present invention, a laser patch and a laser patch treatment set including the same is configured to connect to a user terminal on which an application, which guides a user of the laser patch with an accurate procedure for acupuncture or moxa cautery treatment, which is a Korean medicine treatment, is loaded such that an ordinary user who has no or lacks Korean medicine treatment knowledge may also simply and accurately perform Korean medicine self-treatment.

DESCRIPTION OF REFERENCE NUMERALS

10: Laser Patch Treatment Set
20: Patch Bandage
30: Charger
40: User Terminal
50: Web Server
60: Web Client
100: Laser Patch
110: Patch Body
112: Plate-Shaped Body
113: Lens
115: Operational Light
116: Charging Portion
118: Control Buttons
120: Circuit Board
130: Built-in Battery
140: Low Level Laser Device
150: Sensing Device
152: Contact sensor
154: Temperature Sensor
160: Controller

MODE FOR INVENTION

Advantages and features of the present disclosure and a method of achieving the same will become apparent with reference to the attached drawings and embodiments described below in detail. However, the present invention is not limited to the following embodiments and may be embodied in a variety of different modifications. The embodiments may be provided to completely disclose the present invention and to allow one of ordinary skill in the art to completely understand the scope of the present invention. Throughout the specification, like reference numerals refer to like elements.

The terms used herein are for explaining the embodiments but are not intended to limit the present disclosure. Throughout the specification, unless particularly defined otherwise, singular forms include plural forms. The terms "comprises" and/or "comprising" are used herein as meanings which do not exclude presence or addition of one or more other components, stages, operations, and/or elements in addition to stated components, stages, operations, and/or elements.

Also, the embodiments will be described with reference to cross-sectional views and/or plan views which are exemplary views of the present disclosure. Throughout the drawings, detailed sizes, forms, thicknesses, curvatures, and the like of components are exaggerated or schematized for an effective description on the technical content and may be modified by allowable errors and the like.

Hereinafter, a laser patch and a laser patch treatment set including the same according to one embodiment of the present invention will be described in detail with reference to the attached drawings.

Figure 1:
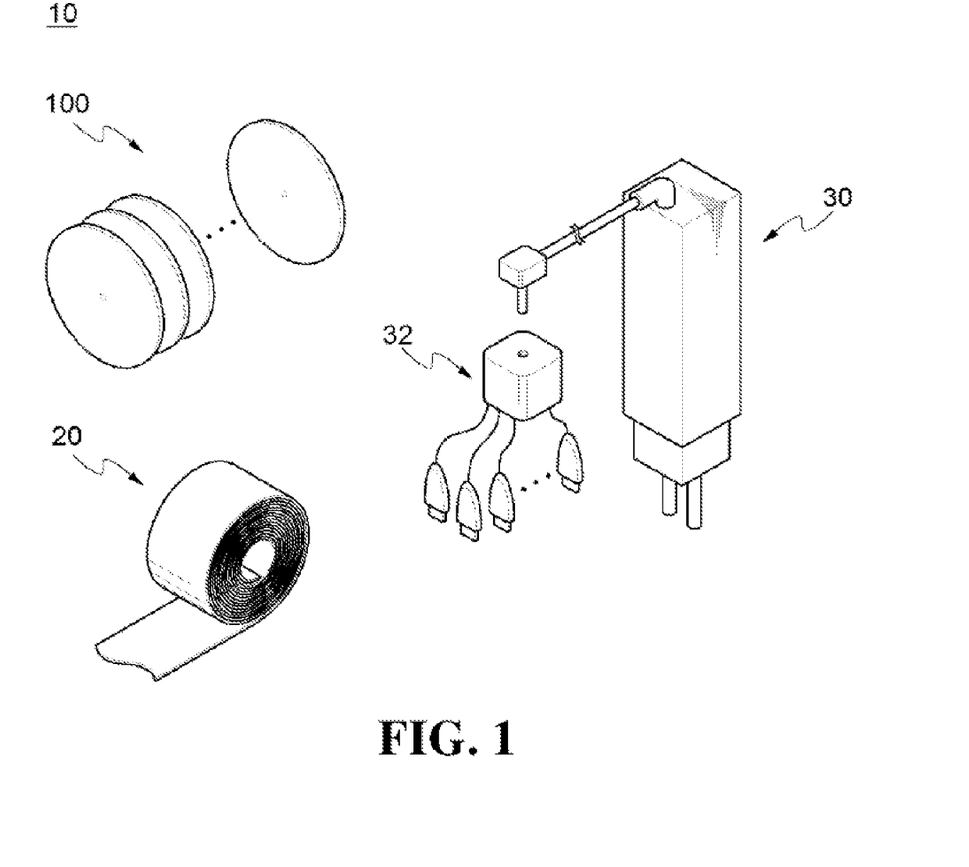
FIG. 1 is a view of a laser patch treatment set according to one embodiment of the present invention.
Figure 2:
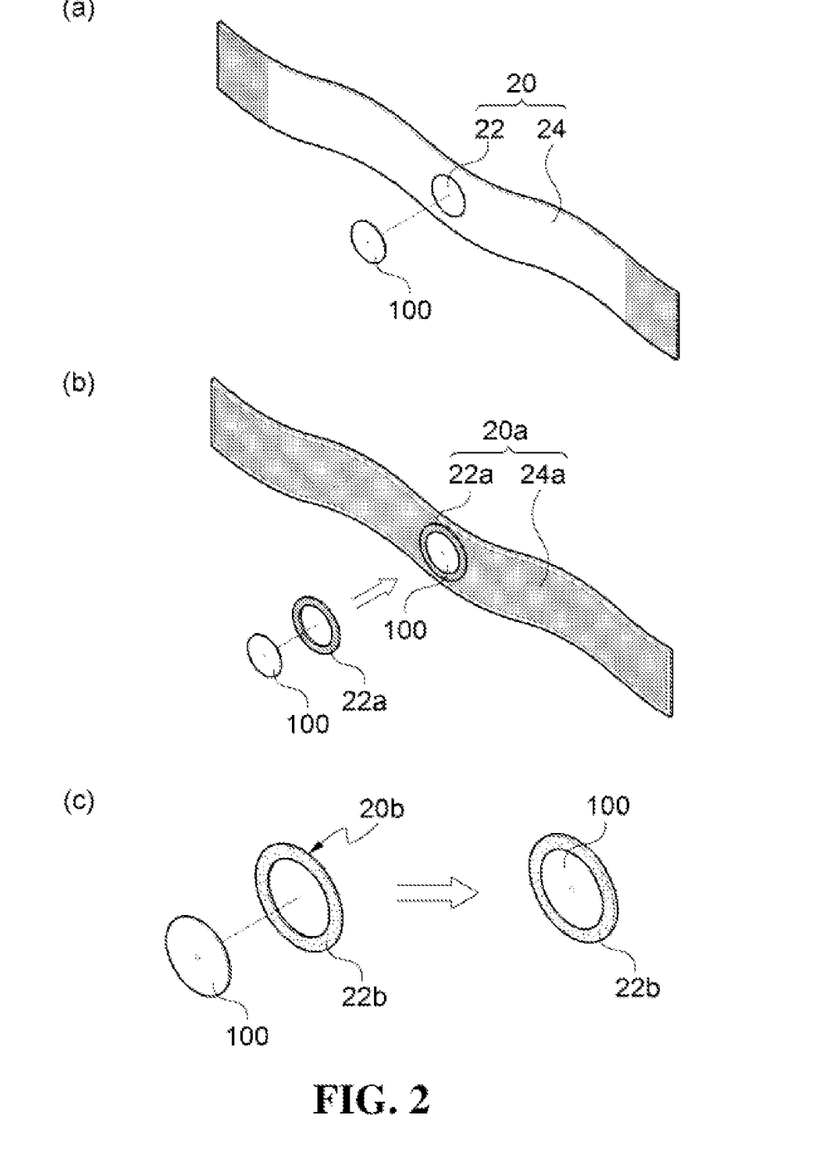
FIG. 2 is a view illustrating a patch bandage of the laser patch treatment set according to one embodiment of the present invention.

FIG. 1 is a view of the laser patch treatment set according to one embodiment of the present invention, and FIG. 2 is a view illustrating a patch bandage of the laser patch treatment set according to one embodiment of the present invention.

Referring to FIGS. 1 and 2, a laser patch treatment set 10 according to one embodiment of the present invention may include a patch bandage 20, a charger 30, a laser patch 100, and a packaging box (not shown) for accommodating and storing the components.

The laser patch 100 may be an apparatus which emits a relatively low level laser, that is, a low level laser (LLL) toward skin. As an example, the laser patch 100 may emit an LLL of about 80 mW or lower. The laser patch 100 may have a relatively small thin plate shape. The laser patch 100 may have a variety of shapes of planes such as a disc-shaped plane, a quadrangular plane, an oval plane, and the like. A plurality of such laser patches 100 are provided in one packaging box such that a user may use a variety of combinations of the plurality of laser patches 100.

The patch bandage 20 may allow the user to fix the laser patch 100 to a desired area on the user's skin. As shown in FIG. 2(a), the patch bandage 20 according to one embodiment of the present invention may include a fixing portion 22 for fixing one laser patch 100 and a bandage portion 24 connected to the fixing portion 22. The bandage portion 24 may dispose the laser patch 100 on the desired area and fix the laser patch 100 to a human body. In this case, the fixing portion 22 is provided as an opening formed in the bandage portion 24 such that the user may insert the laser patch 100 into the fixing portion 22 and then put the bandage portion 24 around the user's body to use.

As shown in FIG. 2(b), a patch bandage 20a according to another embodiment of the present invention may include a fixing portion 22a which has Velcro attached on one surface as form to be fitted onto the laser patch 100 and a bandage portion 24a with Velcro detachably attached to the Velcro of the fixing portion 22a. In this case, the user may attach the fixing portion 22a to the bandage portion 24a at a desired position corresponding to the desired area so as to use the laser patch 100, with which the fixing portion 22a is combined.

As shown in FIG. 2(c), the patch bandage 20b according to still another embodiment of the present invention includes a fixing portion 22b which is used while fitted onto the laser patch 100. Also, an adhesive material capable of adhering to or being in close contact with and being fixed to skin may be applied to one surface of the fixing portion 22b. In this case, the user may closely attach the laser patch 100 to the patch bandage 20b and then may attach the patch bandage 20b to a desired area to use.

The charger 30 may be used for charging the laser patch 100. The charger 30 may include a charging gender 32 which is separate from or integrated with the charger 30 so as to charge a plurality of laser patches 100 at the same time.

Subsequently, the laser patch according to one embodiment of the present invention will be described in detail. Here, a redundant description on the above-described laser patch 100 may be omitted or simplified.

Figure 3:
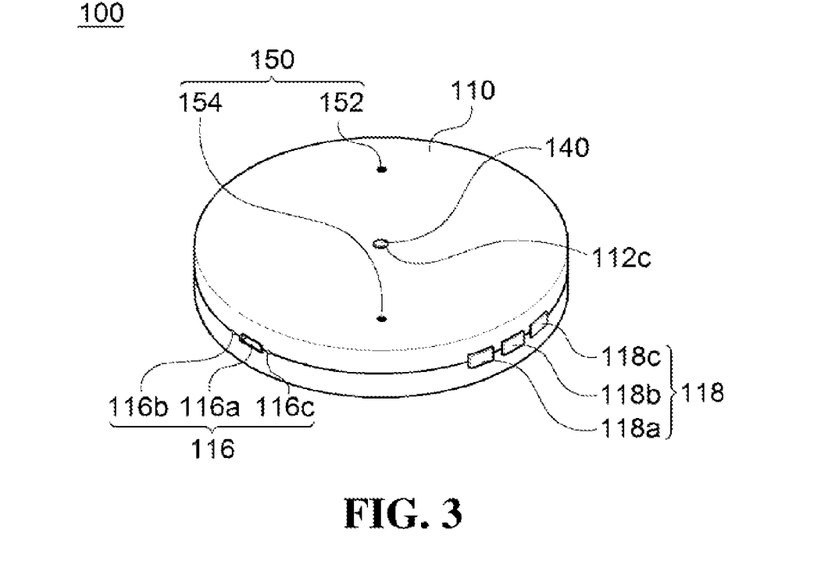
FIG. 3 is a perspective view of a laser patch according to one embodiment of the present invention.
Figure 4:
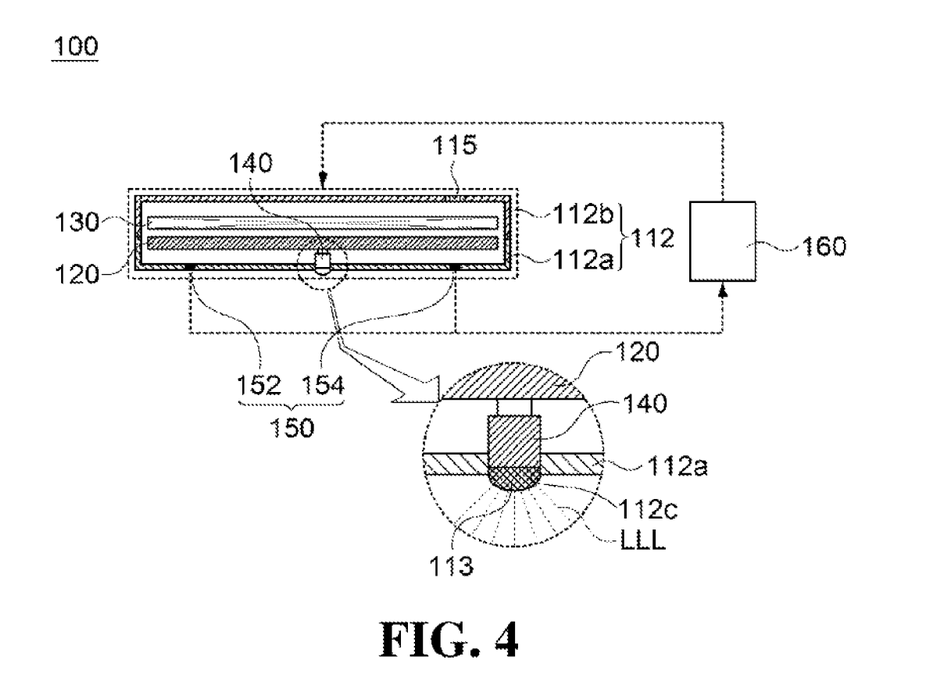
FIG. 4 is a cross-sectional view illustrating components of the laser patch shown in FIG. 3.

FIG. 3 is a perspective view of the laser patch according to one embodiment of the present invention, and FIG. 4 is a cross-sectional view illustrating components of the laser patch shown in FIG. 3.

Referring to FIGS. 3 and 4, the laser patch 100 according to one embodiment of the present invention may include a patch body 110, a circuit board 120, a built-in battery 130, a laser device 140, a sensing device 150, and a controller 160.

The patch body 110 may have a thin plate shape overall and may provide an internal space for protecting, arranging, and supporting the components 120, 130, 140, 150, and 160. As an example, the patch body 110 may include a first body 112a and a second body 112b which are assembled with each other to form a thin plate-shaped body 112. The first body 112a may have one surface which comes into close contact with a human body during treatment, and the second body 112b may have the other surface which is exposed during treatment. A through hole 112c for transmitting an LLL may be provided in the one surface of the first body 112a. The second body 112b may include an operational light 115 which allows the user to recognize emission of the LLL or operation of the laser patch 100.

Meanwhile, a lens 113 for diffusion of the LLL may be further provided in the through hole 112c of the first body 112a. As an example, the lens 113 may be configured to reduce linearity of light of a general laser so as to emit the light toward a wider area in a human body. For this, a convex lens may be used as the lens 113 such that the LLL which passes through the through hole 112c may be transmitted through the lens 113 and then may diffuse so as to penetrate a relatively wide human body area. In this case, it may be suitable for advantageous purposes, that is, pain relief, lymph node stimulation, edema relief, skin stimulation, and the like to dispersedly emit LLLs toward a relatively wide area.

As another example, the lens 113 may be provided to maintain or strengthen linearity of the LLL. For this, a concave lens or a general transmission plate may be used as the lens 113 such that the LLL which passes through the through hole 112c may be transmitted through the lens 113 and then may converge or be maintained so as to penetrate a relatively narrow human body area. In this case, it may be suitable for purposes of blood flow improvement, blood flow strengthening, cell activation, and the like which need intensive emission of the LLL toward a relatively narrow area.

A charging portion 116 may be provided in the patch body 110 for connecting the charger 30 to charge the built-in battery 130. The charging portion 116 may include a charging terminal 116a and a first charge light 116b and a second charge light 116c for allowing recognition of whether or not charging is completed or a residual battery amount. The first charge light 116b may include a green light emitting diode (LED) which indicates completion of charging, and the second charge light 116c may include a red LED which indicates charging.

Also, the patch body 110 may include a variety of control buttons 118 for setting a treatment condition of the laser patch 100. For example, the control buttons 118 may include an on/off button 118a for turning on/off the LLL device 140, a laser level adjusting button 118b for adjusting a laser output intensity of the LLL device 140, and a timer button 118c for setting an operation time of the laser patch 100. The user may set treatment conditions of the laser patch 100 by setting the above-described control buttons 118.

The circuit board 120 may be disposed inside the patch body 110. The circuit board 120 may be disposed to be adjacent to and face the first body 112a in comparison to the built-in battery 130. The circuit board 120 may include at least one printed circuit board (PCB).

The built-in battery 130 may be a battery able to be repeatedly charged. The built-in battery 130 may be charged by the charger 30 and may supply power for laser emission of the LLL device 140 as internal power. A lithium polymer battery may be used as the built-in battery 130 for reducing the risk of explosion and ignition. The built-in battery 130 may allow the laser patch 100 to operate due to its own power without additional external power.

The LLL device 140 may be provided on the circuit board 120 to emit an LLL to the outside through the through hole 112c. A general LLL is known as having a variety of effects such as pain relief, blood flow improvement, blood flow strengthening, cell activation, lymph node stimulation, edema relief, skin stimulation, and the like, and these effects are provided by LLLs having a certain wavelength range. For example, when LLLs are emitted toward a human body for 20 minutes or more as an output of 30 mW or more at a wavelength range of about 630 nm to 680 nm, effects of pain relief, lymph node stimulation, edema relief, cell activation, and the like are relatively high. When LLLs are emitted toward a human body for 20 minutes or more as an output of 30 mW or more at a wavelength range of about 780 nm to 990 nm, effects of blood flow improvement, blood flow strengthening, cell activation, and the like are relatively high. Accordingly, as the LLL device 140, devices having a variety of wavelength ranges may be used according to the above-described purposes.

Here, the above-described LLL device 140 releases much heat outward when generating a laser. The heat of the LLL device 140 may shorten the lifetime of a device, deteriorate the reliability and safety of a product, and particularly, may cause a patient to be burned during treatment. Accordingly, a means capable of effectively releasing heat of the LLL device 140 is necessary. As the means, an additional heat sink (not shown) may be disposed near the LLL device 140. However, in this case, a thickness of the laser patch 100 increases due to at least a degree of protrusion from the circuit board 120. However, the laser patch 100 according to one embodiment of the present invention may have a maximally thin thickness for user convenience. That is, the laser patch may further protrude toward skin as the thickness thereof increases such that a sense of difference or discomfort must increase when the laser patch 100 comes into close contact with the skin and aesthetics thereof are not good.

In order to address the above-described part, the laser patch 100 according to one embodiment of the present invention includes the patch body 110 formed of a material having relatively high thermal conductivity so as to be used as a heat sink for discharging the heat of the LLL device 140 outward or as a heat transfer plate for transferring heat to a human body during treatment. For this, the patch body 110 may include stainless steel, aluminum, copper, and a variety of other metal materials entirely or may include a multilayer structure having a biomaterial in which a skin contact surface is formed of a plastic material which satisfies biocompatibility and an inside thereof is formed of a metal material. In this case, in the laser patch 100, the patch body 110 is partially or entirely heated due to heat generated by the LLL device 140 such that appropriate heat of the patch body 110 is transferred to the human body so as to perform thermal therapy. That is, the above-described laser patch 100 may be configured to perform basic LLL treatment and the thermal therapy using the own heat of the patch body 110 at the same time.

The sensing device 150 may be provided for safety during treatment of the laser patch 100 and provided to appropriately control treatment. For example, the sensing device 150 may include a contact sensor 152 and a temperature sensor 154. The contact sensor 152 may sense whether one surface of the laser patch 100 comes into contact with the user's skin while the laser patch 100 is used. For this, as the contact sensor 152, a pressure sensor, an impedance sensor, a magnetic sensor, a capacitance sensor, and the like may be used. Otherwise, the contact sensor 152 may be a sensor which senses a contact with skin by using a physical or mechanical means. For example, as the contact sensor 152, a physical sensor which is provided with an ordinary protruding pin, and when coming into close contact with the skin, is inserted thereinto and senses whether contact is present.

The temperature sensor 154 may prevent a user from getting burned during treatment because the laser patch 100 is heated by heat generated by the LLL device 140. As described above, the patch body 110 according to one embodiment of the present invention may be formed of a material having relatively high thermal conductivity and may be configured to use heat of the LLL device 140 for thermal therapy. However, in this case, since a burn may occur due to excessive heat generation of the laser patch 110, a safety technique for preventing the occurrence of burns may be necessary. For this, the patch body 110 may include at least one temperature sensor 154 to sense a temperature of the patch body 110. As an example, the temperature sensor 154 may be provided in the first body 112a of the patch body 110 to sense a temperature of the first body 112a which comes into direct contact with a human body during treatment.

The controller 160 may receive a sensing signal from the sensing device 150 and may control the laser patch 100. For example, the controller 160 may receive a contact sensing signal from the contact sensor 152, may turn on the LLL device 140 when the patch body 110 comes into contact with a human body during treatment, and may turn off the LLL device 140 when the patch body 110 does not come into contact with the human body. Also, the controller 160 may receive a temperature sensing signal from the temperature sensor 154, may turn off the LLL device 140 when a temperature of the patch body 110 deviates from a preset temperature, and may turn on the LLL device 140 when the temperature of the patch body 110 satisfies a preset temperature. Here, the preset temperature range may be a temperature range appropriate for thermal therapy. For example, the preset temperature range may be from about 40° C. to 55° C. During treatment, when the patch body 110 is less than about 40° C., a thermal therapy effect may be extremely slight. On the other hand, when the patch body 110 is more than about 55° C., a user may get burned.

Subsequently, an LLL self-treatment method using the above-described laser patch treatment set will be described in detail.

Figure 5:
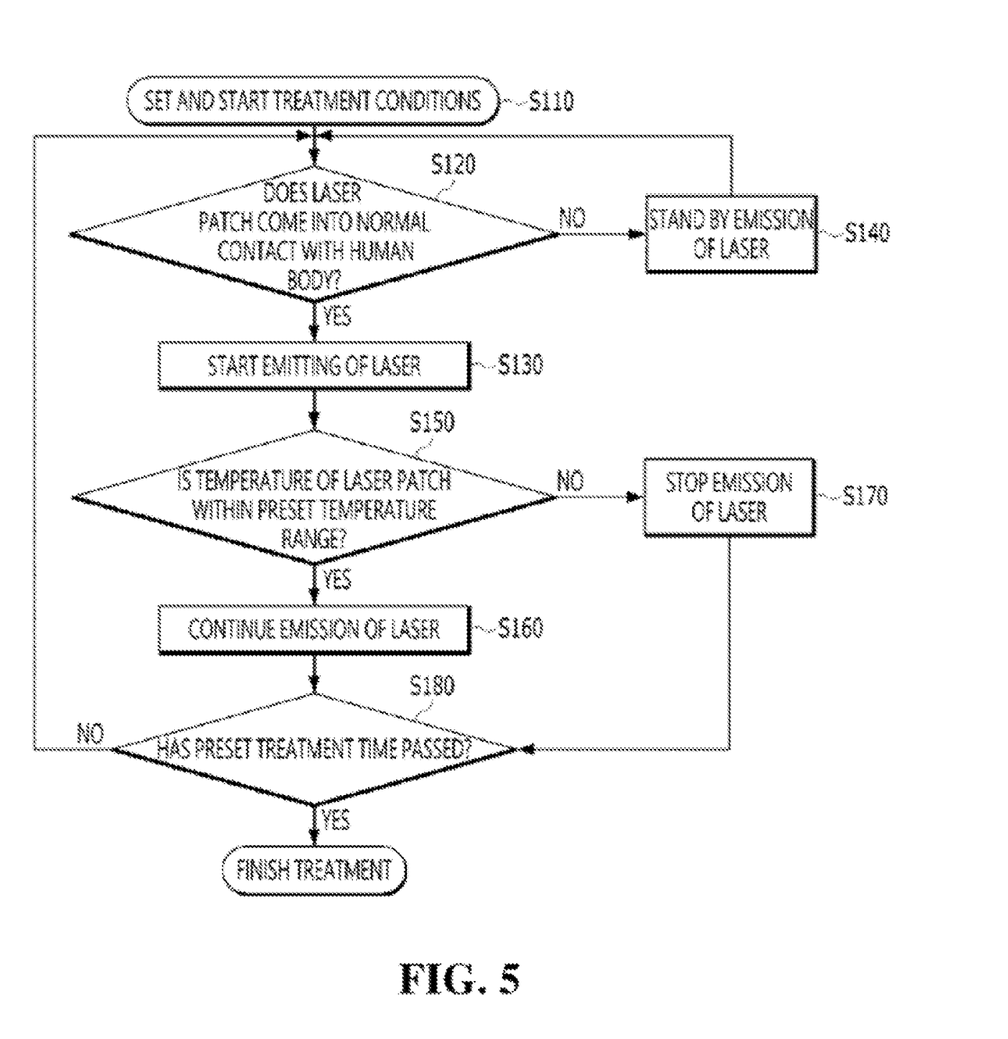
FIG. 5 is a flowchart illustrating a low level laser (LLL) treatment method according to one embodiment of the present invention.

FIG. 5 is a flowchart illustrating an LLL treatment method according to one embodiment of the present invention. Referring to FIGS. 3 to 5, first, treatment conditions may be set and started (S110). In more detail, a user may set an output time and intensity adjustment of an LLL of the laser patch 100 and set whether to perform an operation of turning on (On) by manipulating the control buttons 118 of the laser patch 100. Setting values of the above treatment conditions may differ for each purpose such as pain relief, blood flow improvement, blood flow strengthening, skin regeneration, cell activation, lipolysis, cell stimulation, and the like.

As an example, when a purpose is pain relief, the output of the LLL is set to 40 mW by manipulating the laser level adjusting button 118b, set to 30 minutes by manipulating the timer button 118c, and the laser patch 100 may be turned on by manipulating the on/off button 118a in the above condition. Also, the laser patch 100 may be selected and fixed to the patch bandage 20 which is suitable for skin tissue of a target and then may be attached to an area to be treated.

When the laser patch 100 is attached to the area to be treated, it may be determined whether the laser patch 100 comes into normal contact with a human body (S120). In more detail, the controller 160 may receive a contact sensing signal from the contact sensor 152 of the sensing device 150 and may determine whether one surface of the first body 112a of the laser patch 100 is normally attached to the area to be treated. Here, when it is determined that the patch body 110 comes into normal contact with the area to be treated, the controller 160 may control the circuit board 120 such that the LLL device 140 may start emitting an LLL by using own power of the built-in battery 140 (S130). On the other hand, when it is determined that the patch body 110 does not come into contact with the area to be treated, the controller 160 may cause the LLL emission of the LLL device 14 to be on standby (S140).

That is, the LLL emission of the LLL device 140 may be performed only when the laser patch 100 comes into normal contact with the area to be treated and otherwise may always be on standby in an off state. Accordingly, the laser patch 100 is allowed to emit the LLL only when coming into normal contact with the area to be treated such that it is possible to prevent a negligent accident such as emitting an LLL toward eyes due to the negligence of a user.

Also, when emission of the LLL is performed, it may be determined whether a temperature of the laser patch 100 is within a preset temperature range (S150). In more detail, the controller 160 may receive a temperature sensing signal from the temperature sensor 154 of the sensing device 150 and may determine whether a temperature of the patch body 110 of the laser patch 100 is within the preset temperature range. Here, when the temperature of the patch body 110 is within the preset temperature range, the controller 160 may allow the LLL device 140 to continue the emission of the LLL (S160). On the other hand, when the temperature of the patch body 110 deviates from the preset temperature range, the controller 160 may control the circuit board 120 to stop the LLL emission of the LLL device 140 (S170).

That is, as described above, since the laser patch 100 according to one embodiment of the present invention uses heat of the LLL device 140 as heat for thermal therapy, when the temperature of the patch body 110 excessively increases, a problem such as burns may occur. Accordingly, the above-described laser patch 100 is allowed to emit the LLL only when the temperature does not deviate from a normal temperature range such that safety of treatment may increase.

During a process of performing the above-described laser treatment, it may be determined that a preset treatment time has passed (S180). For example, when 30 minutes which is set in the above-described operation S110 have not passed, the controller 160 may return to the operation S120 and may repeatedly perform the above-described operations S120 to S170. On the other hand, when 30 minutes which is set in the above-described operation S110 have passed, the LLL device 140 is turned off, i.e., the treatment is finished (S190), and then an alarm or external display such as an off light of the operational light 115 may be indicated to allow the user to recognize it.

As described above, the laser patch treatment set 10 according to one embodiment of the present invention includes the laser patches 100 which emit LLLs and the patch bandage 20 capable of fixing the laser patch 100 to the area to be treated. Each of the laser patches 100 may have a relatively small diameter and may have a thin plate shape. In this case, the laser patches 100 may be combined to be selectively arranged in local areas such as a painful area, blood apertures, lymph nodes, and the like such that a variety of self-treatments such as pain relief, blood flow improvement, lymph node stimulation, edema relief, skin stimulation, and the like may be performed. Accordingly, according to the embodiments of the present invention, a laser patch and a laser patch treatment set including the same includes relatively small plate-shaped laser patches to perform treatment in a local area such that the patches may be appropriately combined to fit a necessary treatment type and a desired local area by the user.

Also, according to the embodiments of the present invention, a laser patch 100 and a laser patch treatment set 10 including the same may perform treatments for pain relief, blood flow improvement, blood flow strengthening, skin regeneration, cell activation, lipolysis, cell stimulation, and the like without skin troubles such as a skin rash, an allergy, a burn, and the like which are problems caused by an adhesive and a patch in comparison to general patches or pain relief patches.

Also, according to the embodiments of the present invention, a laser patch 100 and a laser patch treatment set 10 including the same may allow a user to perform self-treatment with the same effect at no additional cost for a long time and prevent resource waste to be eco-friendly in comparison to general patches or pain relief patches.

Subsequently, laser patches according to modified examples of the present invention will be described. Here, a description which overlaps with that of the laser patch 100 according to one embodiment of the present invention may be omitted or simplified.

Figure 6:
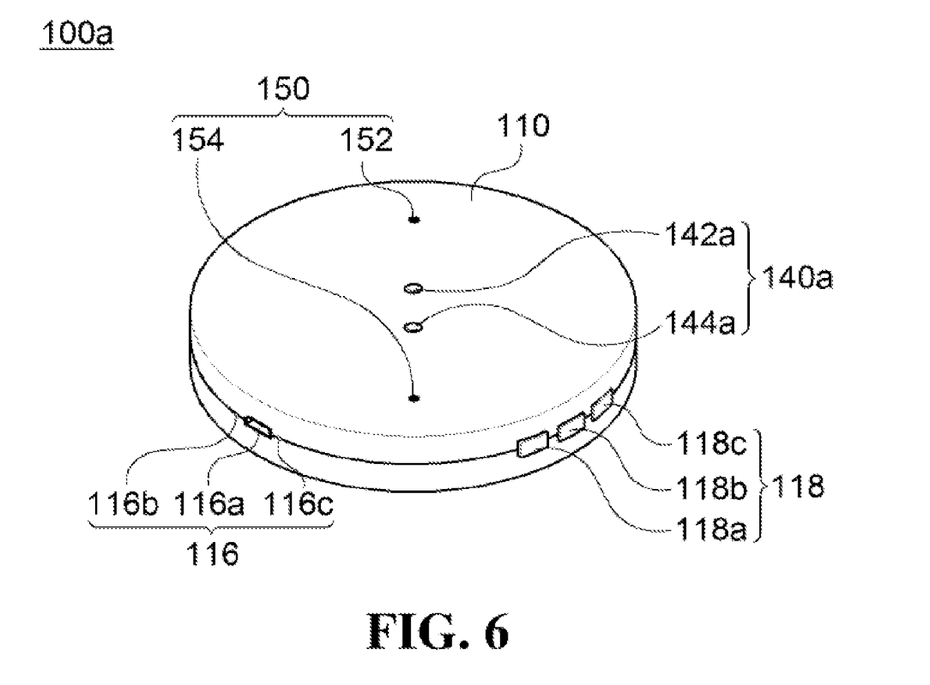
FIG. 6 is a view of a laser patch according to one modified example of the present invention.

FIG. 6 is a view of a laser patch according to one modified example of the present invention. Referring to FIG. 6, a laser patch 100a according to one modified example of the present invention may include the patch body 110, the circuit board 120, the built-in battery 130, an LLL device 140a, the sensing device 150, and the controller 160. The LLL device 140a may include a first device 142a and a second device 144a having different laser wavelength values. As an example, the first device 142a may include an LLL device 140 having a wavelength range of about 630 nm to 680 nm and an output intensity of about 80 mW or less. The first device 142a may be used for purposes such as pain relief, lymph node stimulation, edema relief, cell activation, and the like. On the other hand, the second device 144a may include an LLL device 140 having a wavelength range of about 780 nm to 990 nm and an output intensity of about 80 mW or less. The second device 144a may be used for purposes such as blood flow improvement, blood flow strengthening, cell activation, and the like.

The numbers and arrangements of the first and second devices 142a and 144a may be variously changed. A user may select and control the first and second devices 142a and 144a by manipulating the control buttons 118. For example, when the laser patch 100a is used for pain relief, the user may set the control buttons 118 to turn on only the first device 142a and use the laser patch 100a. Otherwise, when the laser patch 100a is used for blood flow improvement, the user may set the control buttons 118 to turn on only the second device 144a and use the laser patch 100a. When the user intends to use the laser patch 100a for both pain relief and blood flow improvement at the same time, the user may turn on both the first and second devices 142a and 144a and then use the laser patch 100a.

The laser patch 100a having the above-described structure may emit, as one laser patch 100a, lasers having different wavelengths so as to perform laser treatment having two wavelengths by a single laser patch 100a in comparison to the laser patch 100 according to one embodiment of the present invention.

Figure 7:
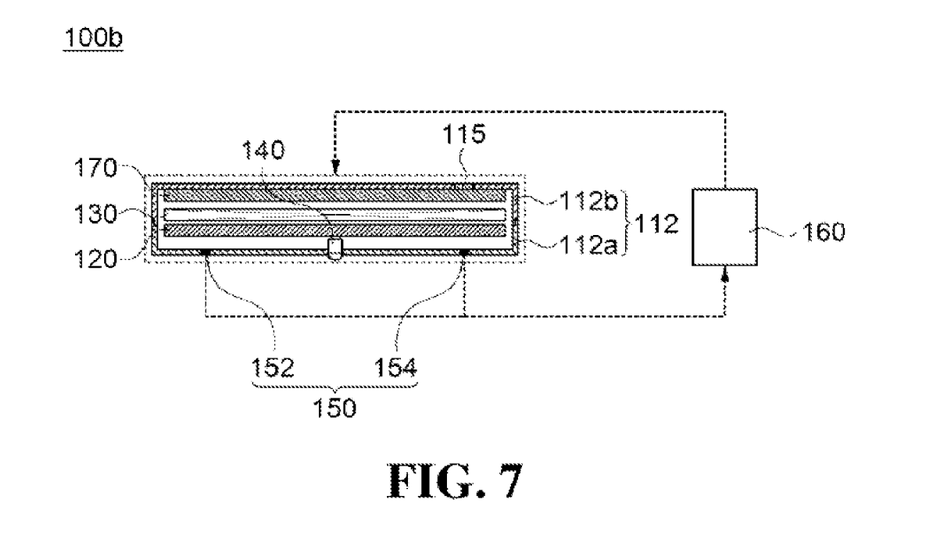
FIG. 7 is a view of a laser patch according to another modified example of the present invention.

FIG. 7 is a view of a laser patch according to another modified example of the present invention. Referring to FIG. 7, a laser patch 100b according to another modified example of the present invention may include the patch body 110, the circuit board 120, the built-in battery 130, the LLL device 140, the sensing device 150, the controller 160, and an oscillator 170. The oscillator 170 may be provided to further add purposes such as blood flow improvement and the like by transferring micro oscillations to an area to be treated during treatment. As the oscillator 170, an ultrasonic oscillator, an electromagnetic motor oscillator, and the like may be used.

The laser patch 100b having the above-described structure may simultaneously or separately perform LLL treatment and micro oscillation treatment as a single laser patch 100b.

Hereinafter, a laser patch and a laser patch treatment set including the same according to another embodiment of the present invention will be described in detail with reference to the attached drawings. Here, a description which overlaps with those of the above-described laser patches 100, 100a, and 100b may be omitted or simplified.

Figure 8:
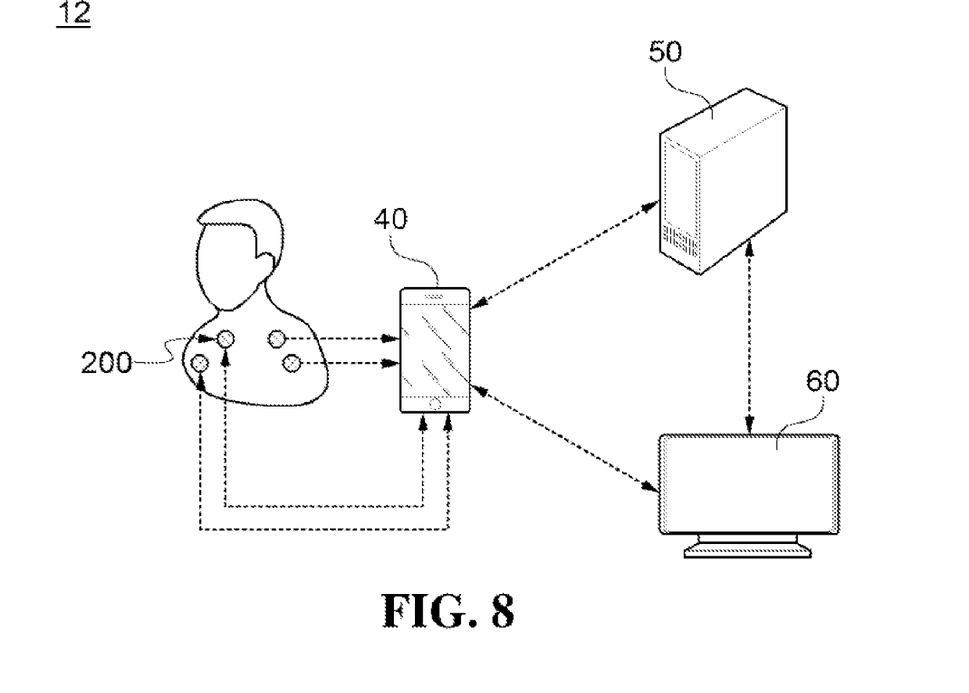
FIG. 8 is a view of a laser patch treatment set according to another embodiment of the present invention.
Figure 9:
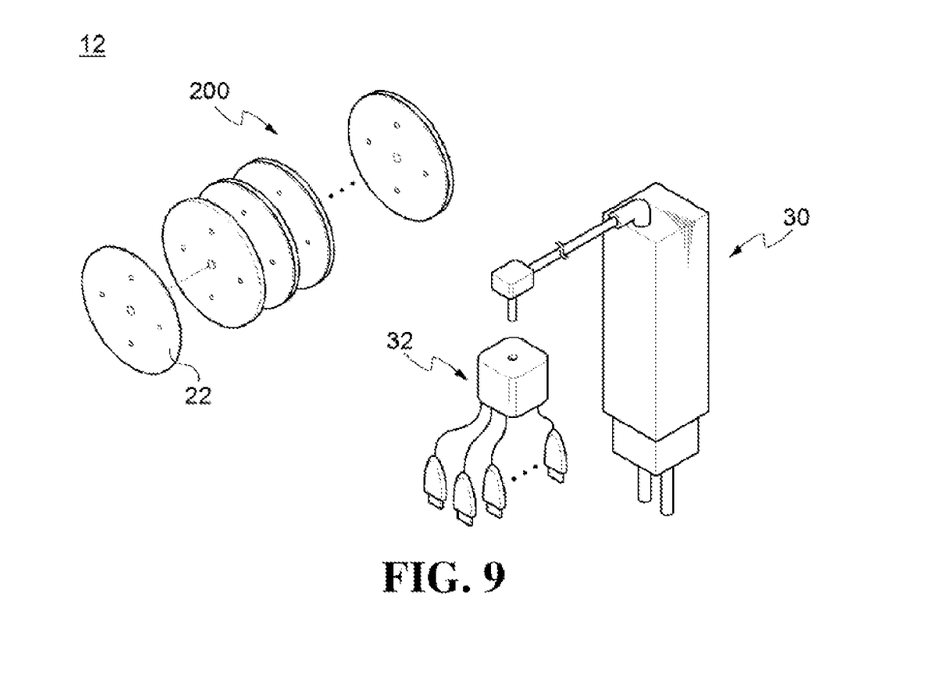
FIG. 9 is a view illustrating a patch bandage of the laser patch treatment set according to another embodiment of the present invention.

FIG. 8 is a view of a laser patch treatment set according to another embodiment of the present invention, and FIG. 9 is a view illustrating a patch bandage of the laser patch treatment set according to another embodiment of the present invention.

Referring to FIGS. 8 and 9, a laser patch treatment set 12 according to another embodiment of the present invention may include a patch bandage 22, the charger 30, a user terminal 40, a web server 50, a web client 60, a laser patch 200, and a packaging box (not shown) for accommodating and storing the components.

The laser patch 200 is an apparatus which emits an LLL toward skin and may have a relatively small thin plate shape. A user may perform self-treatment of Korean medicine treatments such as acupuncture, moxa cautery treatment, and the like by variously combining a plurality of such laser patches 200.

The patch bandage 22 may allow the user to fix the laser patch 200 to a desired area on the user's skin. As shown in FIG. 9, the patch bandage 22 according to another embodiment of the present invention may be provided as an adhesive bandage which is attached to one surface of the laser patch 200. For this, one surface of the patch bandage 22 which comes into contact with skin may be provided as a form to which an adhesive material which is harmless to a human body is applied, and the other surface thereof may be provided as a form which is attached to a laser emission surface of the laser patch 200. The patch bandage 22 may include a plurality of holes formed therein so as not to interfere with a path for lasers emitted by the laser patch 200. During treatment, the user may attach the patch bandage 22 to each of the laser patches 200 and then may allow the patch bandage 22 to come into close contact with desired skin tissue to use.

The charger 30 may be for charging the laser patch 100. The charger 30 may include the charging gender 32 which is separate from or integrated with the charger 30 so as to charge a plurality of such laser patches 200 at the same time.

The user terminal 40 may be a device on which an application for allowing the user to check and control a method of using the laser patch 200, a history, and the like is installed. As the user terminal 40, a variety of portable terminals such as a smart phone and a tablet PC may be used. The user terminal 40 may wirelessly communicate with the laser patch 200 through Bluetooth, Zigbee, radio frequency (RF), and the like. Otherwise, the user terminal 40 may communicate with the laser patch 200 through wires using a USB connection portion and the like. The application may display a variety of pieces of information on LLL treatment such that the user may use the laser patch 200 on the basis of the information.

The web server 50 may include a database including treatment information data on Korean medicine treatments such as basic acupuncture and moxa cautery treatment and may check and manage the database. Also, basic information which is input by the user through the user terminal 40 may be recognized, and the user may be guided with treatment information in the database which is appropriate for the user and the method of using the laser patch 200 through preset conditions and a calculation program.

The web client 60 may receive a variety of pieces of treatment information and the history and data of the laser patch 200 from the user terminal 40 and the web server 50.

Subsequently, the laser patch according to another embodiment of the present invention will be described in detail. Here, a description which overlaps with those of the variously formed laser patches 100, 100a, and 100b may be omitted or simplified.

Figure 10:
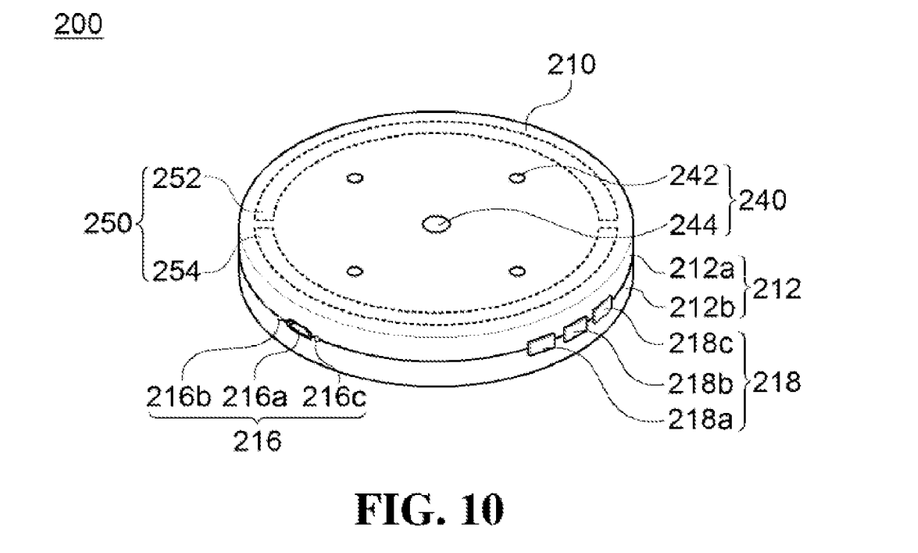
FIG. 10 is a perspective view of a laser patch according to another embodiment of the present invention.
Figure 11:
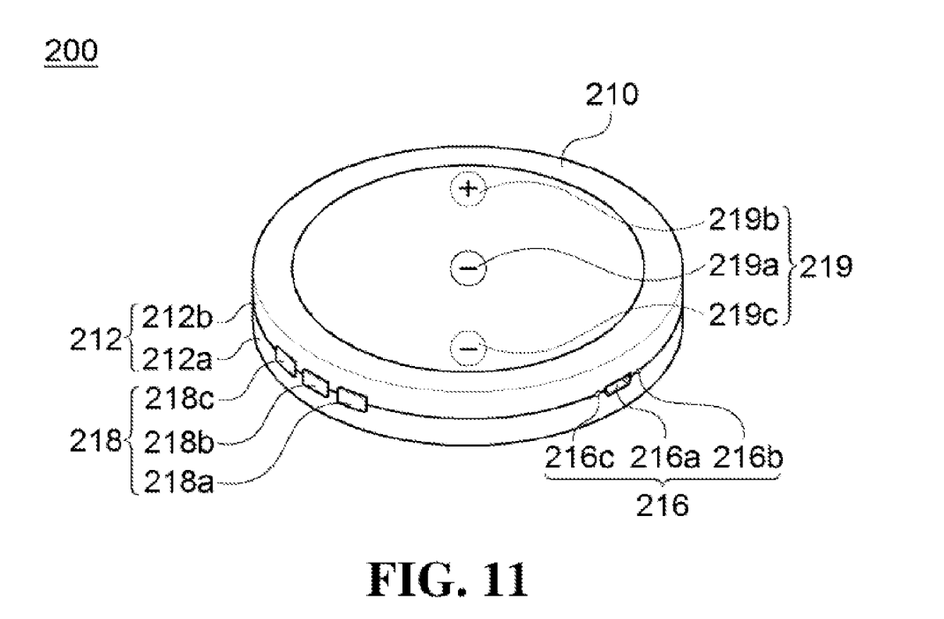
FIG. 11 is a perspective view illustrating the laser patch shown in FIG. 10 when viewed from the other side.

FIG. 10 is a perspective view of a laser patch according to another embodiment of the present invention, and FIG. 11 is a perspective view illustrating the laser patch shown in FIG. 10 when viewed from the other side.

Referring to FIGS. 10 and 11, the laser patch 200 according to another embodiment of the present invention may include a patch body 210, a circuit board (not shown), a built-in battery (not shown), a laser device 240, a sensing device 250, and a controller (not shown). The circuit board, the built-in battery, the controller, and the like may be equal or similar to the components of the above-described laser patches 100, 100a, and 100b.

The patch body 210 may include a first body 212a and a second body 212b which are assembled with each other to form a thin plate-shaped body 212. The first body 212a may have one surface which comes into close contact with a human body during treatment, and the second body 212b may have the other surface which is exposed during treatment. A charging portion 216 may be provided in the patch body 210 for connecting the charger 30 to charge the built-in battery. The charging portion 216 may include a charging terminal 216a and a first charge light 216b and a second charge light 216c for allowing recognition of whether or not charging is completed or a residual battery amount.

The patch body 210 may include a variety of control buttons 218 for setting a treatment condition of the laser patch 200. For example, the control buttons 218 may include the on/off button 218a for turning on/off the LLL device 240, a laser level adjusting button 218b for adjusting a laser output intensity of the LLL device 240, and a timer button 218c for setting an operation time of the laser patch 200. Also, the patch body 210 may further include an oscillator control button 219 for setting and operating an oscillator (not shown) provided in the laser patch 200. For example, the oscillator control button 219 may include an on/off button 219a for turning on/off the oscillator, selecting an oscillation mode, or the like, an increase button 219b for increasing the intensity of the oscillator, and a decrease button 219c for decreasing the intensity of the oscillator. The user may set treatment conditions of the laser patch 200 by setting the above-described control buttons 218 and 219.

The LLL device 240 may include a first device 242 and a second device 244 having different laser wavelength values. As an example, the first device 242 may include an LLL device having a wavelength range of about 630 nm to 680 nm and an output intensity of about 80 mW or less. The first device 242 may be used for purposes such as pain relief, lymph node stimulation, edema relief, cell activation, and the like. On the other hand, the second device 244 may include an LLL device having a wavelength range of about 780 nm to 990 nm and an output intensity of about 80 mW or less. The second device 242 may be used for purposes such as blood flow improvement, blood flow strengthening, cell activation, and the like.

The numbers and arrangements of the first and second devices 242 and 244 may be variously changed. For example, at least one second device 244 may be disposed in a central area of one surface of the patch body 210 and a plurality of such first devices 242 may be arranged in a peripheral area of the one surface of the patch body 210. In the LLL device 240 having the above-described structure, the second device 244 is located above a blood vessel of a user to increase or improve blood flow in a particular blood vessel and the other first devices 242 emit LLLs toward a relatively wide area to relief pain.

The sensing device 250 may be provided for safety during treatment of the laser patch 200 and provided to appropriately control treatment. For example, the sensing device 250 may include a contact sensor 252 and a temperature sensor 254. The contact sensor 252 may sense whether one surface of the laser patch 200 comes into contact with skin of the user when the laser patch 100 is used, and the temperature sensor 254 may prevent the user from getting burned during treatment because the laser patch 200 is heated by heat generated by the LLL device 240.

The controller may receive a sensing signal from the sensing device 250 and may control the laser patch 200. For example, the controller may receive a contact sensing signal from the contact sensor 252, may turn on the LLL device 240 when the patch body 210 comes into contact with a human body during treatment, and may turn off the LLL device 240 when the patch body 210 does not come into contact with the human body. Also, the controller may receive a temperature sensing signal from the temperature sensor 254, may turn off the LLL device 240 when a temperature of the patch body 210 deviates from a preset temperature, and may turn on the LLL device 240 when the temperature of the patch body 210 satisfies a preset temperature.

Subsequently, an LLL treatment process using the above-described laser patch according to another embodiment of the present invention will be described in detail. Here, a description which overlaps with those of the laser patches according to the above-described variety of embodiments may be omitted or simplified.

Figure 12:
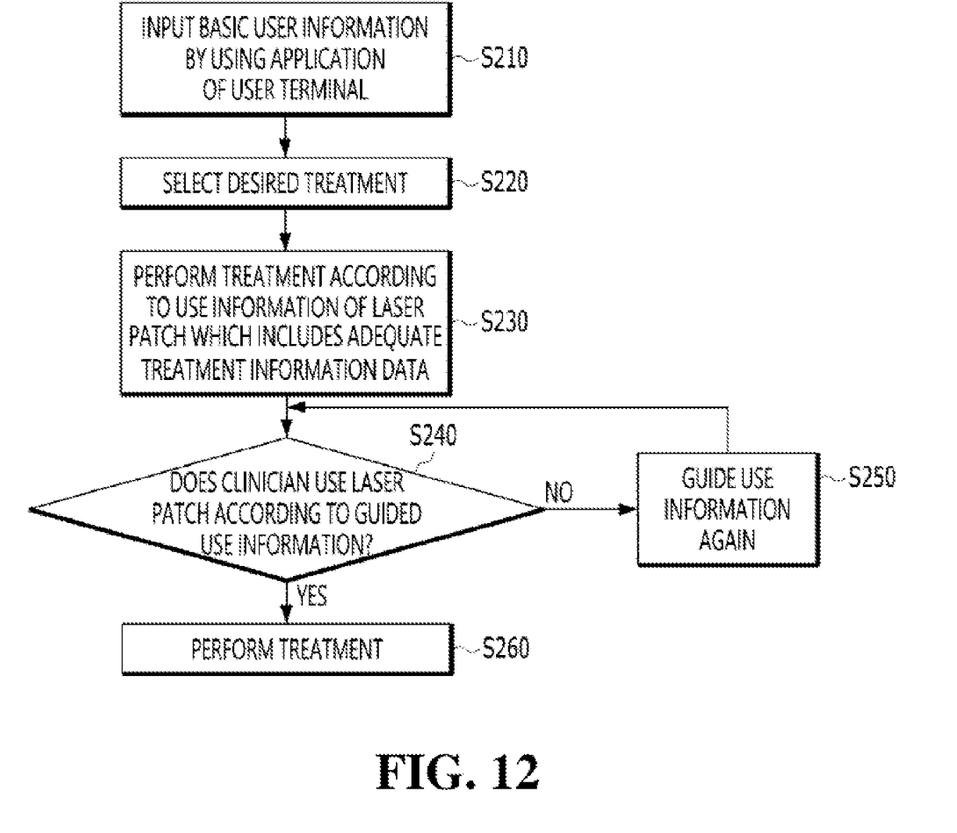
FIG. 12 is a flowchart illustrating a laser treatment method using the laser patch according to another embodiment of the present invention.

FIG. 12 is a flowchart illustrating a laser treatment method using the laser patch according to another embodiment of the present invention. Referring to FIGS. 8 to 12, basic user information may be input by using an application of the user terminal 40 (S210). For example, a user may download a related application through the user terminal 40 and may input basic user items, for example, gender, age, weight, disease to be treated, and the like.

After inputting of the basic user information, the user may select a desired treatment (S220). In more detail, the user may input a treatment item and a position to be treated through the application. For example, when the user inputs pain treatment among pain treatment and blood flow improvement which are classified as major items, treatment areas such as arms, legs, shoulders, waist, and the like which are classified as intermediate items appear. When the shoulders among them are input, a right side, a left side, another detailed painful area, and the like may appear. The user may input the desired treatment and the most appropriate treatment item through the detailed classifications.

Treatment may be performed according to use information of the laser patch including appropriate treatment information data (S230). In more detail, when the user selects the desired treatment, the web server 50 may transmit the appropriate treatment information data from information basically stored in a database, to the user terminal 40. The user may perform the treatment by sequentially attaching the laser patches 200 to an area to be treated according to a method or process of using the laser patches 200 which is shown through the user terminal 40.

Particularly, the treatment information data may include a treatment guide having at least one purposes of pain relief, blood flow improvement, cell activation, cell regeneration, lymph node stimulation, and edema relief such that a treatment sequence and positions are set with respect to the laser patches through the treatment guide selected by previously input information of the user and the user is allowed to sequentially locate the laser patches in the set positions of the user according to the set treatment sequence and positions. Accordingly, the user may perform treatments as Korean medicine acupuncture or a moxa cautery process while sequentially attaching the laser patches 200 to particular positions such that an ordinary person may easily perform specialized Korean medicine self-treatment.

It may be determined whether a clinician uses the laser patches according to the guided use information in the above-described treatment process (S240). For example, the controller (not shown) may determine whether the user performs the treatment according to the treatment process guided through the user terminal 40 on the basis of whether the laser patch 200 comes into contact with a human body when the user attaches the laser patch 200 to the human body which is transmitted from the sensing device 250. When the user performs the treatment by using the laser patches 200 according to the guided treatment process, it is determined to be normal use such that normal treatment may be performed (S260). Here, the normal treatment may include an LLL treatment which has been described above with reference to FIG. 5. On the other hand, when the user does not perform the treatment by using the laser patches 200 according to the guided treatment process, the user may be notified of it and the use information may be guided again so as to perform appropriate treatment (S250).

As described above, the laser patch 200 and the laser patch treatment set 12 including the same according to another embodiment of the present invention may include the laser patches 200 which perform LLL treatments, the user terminal 40 on which the application which communicates with the laser patches 200 and guides the method and process of using the laser patches 200 is installed, and the web server 50 connected to the user terminal 40 such that an ordinary user may be guided with a desired treatment procedure by using the application and may perform Korean medicine self-treatment by using the laser patches 200. Accordingly, according to the embodiments of the present invention, there are provided a laser patch and a laser patch treatment set including the same which are configured to connect to a user terminal on which an application which guides a user of the laser patches with an accurate procedure for acupuncture or moxa cautery treatment, which is a Korean medicine treatment, is loaded such that an ordinary user who has no or lacks Korean medicine treatment knowledge may simply and accurately perform Korean medicine self-treatment.

Although the laser patch and the laser patch treatment set including the same according to the detailed embodiments of the present invention have been described, it is obvious that a variety of modifications may be made without departing from the scope of the present invention. Therefore, the scope of the present invention should not be limited to the above-described embodiments and should be determined by the following claims and equivalents thereof. The above-described embodiments should be understood as being exemplary and not limitative in every aspect. The scope of the present invention is defined by the following claims rather than the detailed description. It should be understood that all changes and modifications derived from the meaning, scope, and equivalents of the claims are included in the scope of the present invention.

The invention claimed is:

1. A wearable multi-wavelength laser therapy device that is effective in treating joint pain and arthritis by a selective action of cell regeneration and blood flow improvement, the wearable multi-wavelength laser therapy device comprising:
   a patch body;
   a plurality of laser diode devices configured to emit low-power lasers with different wavelengths to one surface of the patch body; and
   a controller configured to control the laser diode devices such that unique actions for each wavelength of the laser diode devices are selectively performed,
   wherein a device with a relatively high wavelength among the laser diode devices is arranged to a central region of the patch body compared to a device with a relatively low wavelength to apply the low-power laser with the relatively high wavelength to the central region of the patch body which faces a skin during treatment, and
   wherein the controller selectively controls a group of devices with the relatively high wavelength and a group of devices with the relatively low wavelength to simultaneously or alternately perform at least two or more actions.

2. The wearable multi-wavelength laser therapy device of claim 1, wherein
   the plurality of laser diode devices include a first device and a second device,
   the first device emits a low-power laser in a wavelength range of 630 nm to 680 nm for at least one of pain relief, lymph node stimulation, edema relief, and cell activation,
   the second device emits a low-power laser in a wavelength of 780 nm to 990 nm for at least one of the blood flow improvement and blood flow enhancement, and
   the second device is placed on an operator's blood vessel to promote or improve blood flow of the blood vessel such that a pain-inducing factor in a laser diode device site is rapidly discharged from a pain site.

3. The wearable multi-wavelength laser therapy device of claim 1, wherein
   the plurality of laser diode devices include a first device and a second device,
   the first device emits a low-power laser in a wavelength range of 630 nm to 680 nm for at least one of pain relief, lymph node stimulation, edema relief, cell activation, and cell regeneration,
   the second device emits a low-power laser in a wavelength of 780 nm to 990 nm for at least one of the blood flow improvement and blood flow enhancement,
   a vibrator configured to generate vibration energy is provided in the patch body, and
   the vibrator is provided to further add effects of the cell regeneration by the first device or the blood flow improvement by the second device.

4. The wearable multi-wavelength laser therapy device of claim 1, wherein
   the patch body is used as a heat sink for dissipating heat generated from the plurality of laser diode devices to an outside of the patch body, and
   the controller stops laser emission of at least one of the plurality of laser diode devices when a temperature of the heat sink exceeds a preset temperature range.

5. The wearable multi-wavelength laser therapy device of claim 1, wherein
   the patch body includes a plurality of patch bodies such that a user uses a combination of the plurality of patch bodies according to a type of treatments required by the user and a desired local site.

6. The wearable multi-wavelength laser therapy device of claim 1, wherein
   the controller includes a smartphone application that enables a user to adjust treatment condition setting values such that treatment suitable for a therapy desired by the user is performed according to a treatment method and a treatment image guided by the smartphone application.

* * * * *